United States Patent
Kingston et al.

(10) Patent No.: US 10,254,419 B2
(45) Date of Patent: Apr. 9, 2019

(54) ACQUISITION AND PROCESSING OF DATA IN A TOMOGRAPHIC IMAGING APPARATUS

(71) Applicant: FEI Company, Hillsboro, OR (US)

(72) Inventors: Andrew Kingston, Kambah (AU); Shane Latham, Griffith (AU); Adrian Sheppard, Fisher (AU); Glenn Myers, Waramanga (AU); Benoit Recur, Turner (AU); Heyang Li, Harrison (AU); Trond Karsten Varslot, Vuku (NO)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/237,309

(22) Filed: Aug. 15, 2016

(65) Prior Publication Data
US 2017/0052264 A1    Feb. 23, 2017

(30) Foreign Application Priority Data
Aug. 17, 2015 (EP) .................................. 15181202

(51) Int. Cl.
*G01T 1/29* (2006.01)
*G06T 11/00* (2006.01)
(Continued)

(52) U.S. Cl.
CPC ......... *G01T 1/2985* (2013.01); *G01N 23/046* (2013.01); *G01N 23/2204* (2013.01);
(Continued)

(58) Field of Classification Search
CPC .......... G01N 2223/419; G01N 23/046; G01N 2223/418; G01N 23/02; G06T 11/003;
(Continued)

(56) References Cited

U.S. PATENT DOCUMENTS 5,090,245 A  * 2/1992 Anderson ............. G01S 7/6245
                                                     73/625
2006/0038127 A1* 2/2006 Furukawa ............... H01J 37/26
                                                     250/311
(Continued)

FOREIGN PATENT DOCUMENTS

WO    WO2013049888 A1 *  4/2013

OTHER PUBLICATIONS

Jia, Xun, et al. "GPU-based iterative cone-beam CT reconstruction using tight frame regularization." Physics in medicine and biology 56.13 (2011): 3787.*

(Continued)

*Primary Examiner* — Wyatt A Stoffa
(74) *Attorney, Agent, or Firm* — Scheinberg & Associates, P.C.; Michael O. Scheinberg

(57) ABSTRACT

A method of investigating a specimen using a tomographic imaging apparatus using a stage for producing relative motion of a source with respect to a specimen, so as to allow the source and a detector to image the specimen along a series of different viewing axes and a processing apparatus for assembling a tomographic image of at least part of the specimen. The investigation is carried out by considering a virtual reference surface that surrounds the specimen and is substantially centered thereon, considering an incoming point of intersection of each of said viewing axes with this reference surface, thereby generating a set of such intersection points corresponding to the series of viewing axes, choosing discrete viewing axes in the series so as to cause the set to comprise a two-dimensional lattice of points located areally on the reference surface in a substantially uniform distribution.

20 Claims, 8 Drawing Sheets

(51) Int. Cl.
G01N 23/046 (2018.01)
G01N 23/2204 (2018.01)
H01J 37/22 (2006.01)

(52) U.S. Cl.
CPC .......... *G06T 11/005* (2013.01); *H01J 37/222* (2013.01); *G06T 2211/436* (2013.01); *H01J 2237/2807* (2013.01)

(58) Field of Classification Search
CPC .......... G06T 2207/10056; G06T 11/005; H01J 2237/2611; H01J 37/222; G01T 1/2985
See application file for complete search history.

(56) References Cited

U.S. PATENT DOCUMENTS

| | | | | |
|---|---|---|---|---|
| 2013/0235971 | A1* | 9/2013 | Oreper | G01T 1/2985 378/19 |
| 2014/0145077 | A1* | 5/2014 | Schoenmakers | G01N 23/2251 250/307 |
| 2014/0233691 | A1* | 8/2014 | Sheppard | G01N 23/046 378/4 |
| 2015/0351705 | A1* | 12/2015 | Brady | G01N 23/046 378/20 |
| 2016/0307729 | A1* | 10/2016 | Lazic | H01J 37/222 |

OTHER PUBLICATIONS

Sidky, Emil Y., Yu Zou, and Xiaochuan Pan. "Minimum data image reconstruction algorithms with shift-invariant filtering for helical, cone-beam CT." Physics in Medicine and Biology 50.8 (2005): 1643.*
"Cone Beam Computed Tomography", Wikipedia, Retrieved from the Internet Aug. 4, 2016, https://en.wikipedia.org/wiki/Cone_beam_computed_tomography, 8 pages.
"Electron Microscope", Wikipedia, Retrieved from the Internet Oct. 15, 2015, http://en.wikipedia.org/wiki/Electron_microscope, 11 pages.
"Focused Ion Beam", Wikipedia, Retrieved from the Internet Jul. 11, 2016, https://en.wikipedia.org/wiki/Focused_ion_beam, 7 pages.
"Nanotomography", Wikipedia, Retrieved from the Internet Aug. 4, 2016, from https://en.wikipedia.org/wiki/Nanotomography, 1 page.
"Scanning Electron Microscope", Wikipedia. Retrieved from the Internet Jul. 25, 2016, http://en.wikipedia.org/wiki/Scanning_electron_microscope, 23 pages.
"Scanning Helium Ion Microscope", Wikipedia, Retrieved from the Internet on Jul. 25, 2016, http://en.wikipedia.org/wiki/Scanning_Helium_Ion_Microscope, 2 pages.
"Scanning Transmission Electron Microscopy", Wikipedia, Retrieved from the Internet Jul. 25, 2016, http://en.wikipedia.org/wiki/Scanning_transmission_electron_microscopy, 5 pages.
"Spiral Computed Tomography", Wikipedia, Retrieved from the Internet Aug. 4, 2016, https://en.wikipedia.org/wiki/Spiral_computed_tomography, 2 pages.
"Transmission Electron Microscopy", Wikipedia, Retrieved from the Internet Jul. 25, 2016, http://en.wikipedia.org/wiki/Transmission_electron_microscopy, 23 pages.
"X-Ray Microtomography", Wikipedia, Retrieved from the Internet Aug. 4, 2016, https://en.wikipedia.org/wiki/X-ray_microtomography, 5 pages.
Abbas, S., et al., "Effects of sparse sampling schemes on image quality in low-dose CT," Med Phys., Nov. 2013, 12 pages, vol. 40, No. 11.
Escovitz, W.H. et al., "Scanning Transmission Ion Microscope with a Field Ion Source," Proc. Nat. Acad. Sci. USA, May 1975, pp. 1826-1828, vol. 72, No. 5.
Hu, Y., et al." L0 constrained sparse reconstruction for multi-slice helical CT reconstruction", Physics in Medicine and Biology, Feb. 1, 2011, pp. 1-19, vol. 56, No. 4, 2011 Institute of Physics and Engineering in Medicine.
Kudo, H., et al. "Image reconstruction for sparse-view CT and interior CT—introduction to compressed sensing and differentiated backprojection", QIMIMAS, Jun. 5, 2013, pp. 147-152, vol. 3, No. 3. AME Publishing Company.
Neuser, E., et al. "NanoCT® Visualizing internal 3D structures with submicrometer resolution", DIR 2007, 18 p, vol. 39 Issue 41,International symposium on digital industrial radiology and computed tomography, France.
Varentsov, D. et al. "First biological images with high-energy proton microscopy", Physica Medica (2013), pp. 208-213, vol. 29.

* cited by examiner

ACQUISITION AND PROCESSING OF DATA IN A TOMOGRAPHIC IMAGING APPARATUS

The invention relates to a method of investigating a specimen using a tomographic imaging apparatus comprising:

A specimen holder, for holding the specimen;

A source, for producing a beam of radiation that can be directed at the specimen;

A detector, for detecting a flux of radiation transmitted through the specimen from the source;

A stage apparatus, for producing relative motion (positioning) of the source with respect to the specimen, so as to allow the source and detector to image the specimen along a series of different viewing axes;

A processing apparatus, for assembling output from the detector into a tomographic image of at least part of the specimen.

The invention also relates to a tomographic imaging apparatus that can be used in performing such a method.

The invention further relates to a charged-particle microscope provided with such a tomographic imaging apparatus.

In tomographic imaging (also referred to as Computed Tomography (CT)) as referred to above, the source and (diametrically opposed) detector are used to look through the specimen along different lines of sight (viewing axes), so as to acquire penetrative observations of the specimen from a variety of perspectives; these are then used as input to a mathematical procedure that produces a reconstructed "volume image" of (part of) the (interior of) the specimen. In order to achieve a series of different lines of sight as alluded to here, one can, for example, choose to:

(a) Keep the source and detector static and move the specimen relative to them;

(b) Keep the specimen static and move the source relative to it. In this case, one can elect to:

Move the detector in synchronization with the source; or

Embody the detector as a (static) array of sub-detectors, with positions matched to correspond to the different positions to be assumed by the source.

Regardless of whether the source or specimen is moved, it is possible to describe their relative motion using (for example) a specimen-centric coordinate system/reference frame. The beam of radiation that traverses the specimen can, for example, be regarded as being cone-like (thus yielding so-called cone beam tomography) or resembling a segment of a disc (thus yielding so-called fan beam tomography), depending on the geometry/shape that the detector "presents" to the source; a parallel/collimated beam is also possible. The "viewing axis" alluded to here can be regarded as corresponding to an "optical axis" along which the beam (from source through specimen to detector) propagates; it basically corresponds to the position of a central/median/core ray in that beam. In order to achieve sufficient sample penetration, the employed radiation will generally comprise X-rays.

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT", in which a micro-focused source is used to image microscopic specimens, e.g. in geology/petrology, biological tissue studies, etc. Continuing this drive toward ever-greater resolution, so-called "nano CT" instruments have also been developed; these may be standalone tools, but, for example, they may also be embodied as (add-on) modules for (a vacant vacuum/interface port of) a charged-particle microscope (CPM), in which case the CPM's charged-particle beam is used to irradiate a metal target, causing production of the Bremsstrahlung X-rays used to perform the desired tomography (see FIG. 4B, for example). More information on (some) of these topics can, for example, be gleaned from the following references:

https://en.wikipedia.org/wiki/X-ray microtomography https://en.wikipedia.org/wiki/Nanotomography http://www.ndt.net/article/dir2007/papers/24.pdf It should be noted that, as referred to here in the context of a CPM, the phrase "charged particle" should be broadly construed as encompassing:

Electrons, as in the case of a Transmission Electron Microscope (TEM), Scanning Electron Microscope (SEM), and Scanning Transmission Electron Microscope (STEM), for instance. See, for example, the following references:

http://en.wikipedia.org/wiki/Electron_microscope http://en.wikipedia.org/wiki/Scanning_electron_microscope http://en.wikipedia.org/wiki/Transmission_electron_microscopy http://en.wikipedia.org/wiki/Scanning_transmission_electron_microscopy Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc. See, for example, the following references:

https://en.wikipedia.org/wiki/Focused_ion_beam http://en.wikipedia.org/wiki/Scanning_Helium_Ion_Microscope W. H. Escovitz, T. R. Fox and R. Levi-Setti, Scanning Transmission Ion Microscope with a *Field Ion Source*, Proc. Nat. Acad. Sci. USA 72(5), pp 1826-1828 (1975).

Other charged particles, such as protons and positrons, for instance. See, for example, the following reference:

http://www.ncbi.nlm.nih.gov/pubmed/22472444

It should also be noted that, in addition to imaging and/or surface modification, a charged particle beam in a CPM may also have other functionalities, such as performing spectroscopy, examining diffractograms, etc.

As regards the specimen/source relative motion employed to achieve different lines of sight/viewing axes, use is conventionally made of:

A circular scan, in which the source follows a planar orbit about the specimen, and images are captured at a very high sampling rate (i.e. quasi-continuously) along this orbit. This type of scan can be applied in situations where only a relatively thin "slice" of a specimen has to be imaged, e.g. when making a cone beam CT scan of human dentition. See, for example, the following reference:

https://en.wikipedia.org/wiki/Cone_beam_computed_tomography

A helical scan, in which the source follows a coil-like (spiral) path about a (longitudinal) axis of the specimen, and images are again captured at a very high sampling rate (i.e. quasi-continuously) along this path. This type of scan can be applied in situations where a relatively elongated portion of a specimen has to be imaged, e.g. when making a CT scan of (a portion of) a human vertebral column. It is typically achieved by combining circular motion (e.g. of the source) and concurrent translational motion (e.g. of the specimen). See, for example, the following reference:
https://en.wikipedia.org/wiki/Spiral_computed_tomography Although prior-art techniques such as these have produced tolerable results up to now, the current inventors have worked extensively to provide an innovative alternative to the conventional approach. The results of this endeavor are the subject of the current invention.

It is an object of the invention to provide an innovative tomographic imaging technique. More specifically, it is an object of the invention that this technique should employ a radically different data acquisition strategy as compared to known techniques. Moreover, it is an object of the invention that this new acquisition strategy should admit use of novel data processing techniques.

These and other objects are achieved in a method as set forth in the opening paragraph above, which method is characterized by the following steps:
- Considering a virtual reference surface that surrounds the specimen and is substantially centered thereon;
- Considering an incoming point of intersection of each of said viewing axes with this reference surface, thereby generating a set of such intersection points corresponding to said series of viewing axes;
- Choosing discrete viewing axes in said series so as to cause said set to comprise a two-dimensional lattice of points located areally on said reference surface in a substantially uniform distribution.

Reference to FIGS. 1 and 3—and comparison to FIG. 2—will help clarify these aspects. It should also be noted that the terms "areal" and "areally" are, respectively, the adjective and adverb of "area".

The current invention differs fundamentally from the prior art in the manner in which the specimen is sampled, i.e. in the manner in which a measurement set (comprising "raw" images captured along different sampling/viewing axes, and used as input to achieve the reconstructed tomographic output) is spatially acquired. Rather than employing an essentially continuous progression of sampling points that are concentrated/clustered along a scanning tract—such as a circle or helix—it instead employs a discrete lattice (network, array, web, matrix) of sampling points, which is areal (two-dimensional) rather than curvilinear (one-dimensional) in nature/geometry; accordingly, the sampling points (abovementioned intersection points) according to the invention are distributed substantially uniformly (homogeneously) across said virtual reference surface, as opposed to the prior art, in which their relatively cluttered arrangement on a curve is intrinsically non-uniform (inhomogeneous, and highly isotropic along the preferential direction defined by the course of the curve). It should be noted in this context that a "substantially uniform" distribution does not necessarily imply a "regular" distribution: the lattice distribution in the present invention may be regular (being a formal repeating array of a basic unit cell; see FIG. 3A, 3B or 3D, for example), or irregular (as in the case of a (quasi-)random sprinkling of points; see FIG. 3C, for example), since both of these situations distribute sampling points in an areal manner instead of concentrating them along a sampling tract (see FIG. 2, for example). For illustration purposes, somewhat of an analogy can be made here to the act of applying granulate fertilizer to a lawn, whereby:

- In the prior-art analogy, the fertilizer is applied along one or more thin lines, leading to an overdose of fertilizer along the lines and fertilizer starvation between the lines;
- Using the inventive approach, the fertilizer is spread uniformly across the lawn; whether according to a strict matrix or a less formal scattering, the result is still a more uniform coverage of the lawn by the granules, with no (structural) overdosing or under-dosing.

As a result of the fundamental differences set forth in the previous paragraph, the following important advantages can be achieved:

(i) More uniform/isotropic sampling:
By nature, a sampling tract such as a circle or helix will have a high sampling density along one direction (the course followed by the tract), and much lower/zero sampling density along other directions (outside said course). Accordingly, a relatively large portion of the specimen will be proportionally under-sampled, whereas the remaining relatively small portion thereof (along the scanning tract) will be proportionally over-sampled. The present invention obviates this problem, by employing a sampling lattice that is substantially areally uniform.

(ii) Homogenized mean density of rays through the specimen/homogenized resolution:
If one considers a cone of rays moving from the source through the specimen and then onto the detector, a given point in the specimen will be impinged upon by a ray in a particular (angular) region of this cone. In a helical sampling strategy, successive source positions along the helix will cause said point to be impinged upon by rays in different (angular) regions of successive radiation cones; accordingly, the mean density of rays through the specimen will be anisotropic. In contrast, the uniform sampling strategy of the present invention mitigates this (undesirable) effect, and produces a substantially isotropic mean density of rays through the specimen. This homogenizes resolution in the reconstructed imagery. Put another way: it reduces/minimizes non-uniform magnification in the obtained tomogram.

(iii) Smaller input data set:
Because prior-art sampling strategies drastically over-sample (parts of) the imaged specimen along the sampling tract that they employ, they implicitly entail use of a wastefully large input data set, with an attendant excessively large calculation overhead (to construct an associated tomogram). This issue tends to become increasingly pronounced with increasing fan/cone angle. The more uniform sampling strategy of the present invention allows a much smaller data set to be used as input, with an associated (substantial) reduction in calculation overhead.

(iv) Homogenized Point Spread Function in reconstruction space:
The effect alluded to in (i) results in a more uniform/homogeneous/isotropic (shift-invariant) imaging Point Spread Function (PSF) in the mathematical "tomographic space" in which reconstruction occurs. This allows the reconstruction process to be performed using mathematical tools that cannot (practically) be employed in prior-art techniques. More specifically, it allows certain iterative reconstruction and pre-conditioning filtering techniques to be employed so as to accelerate convergence in the reconstruction process, thereby significantly reducing computational overhead/ complexity. These techniques include post-back-projection Space-Invariant Filtering (SIF), and Multi-Grid Iterative Reconstruction (MGIR), which will be explained in greater detail below.

(v) Sparse sampling:

The uniform distribution of sampling points in the inventive approach lends itself to so-called sparse sampling strategies, e.g. by increasing the distance between neighboring/proximal points in the lattice. Such strategies cannot be (so easily) achieved in prior-art techniques.

These aspects of the invention will be elucidated in greater detail below.

In a particular embodiment of the present invention, the aforementioned lattice of sampling points has a geometry selected from the group comprising:

An orthogonal array;
A skewed orthogonal array;
A staggered orthogonal array;
A hexagonal array, and combinations hereof. In their purest form, all such lattice geometries/layouts can be considered as "regular", in that they can be assembled as repetitions of a basic "unit cell" (see, for example, (quadrilateral) unit cell M' in FIGS. 3A, 3B and 3D). In reality, they will typically be somewhat distorted from their purest geometry (but will still form a very good/recognizable approximation thereto) by drift effects occurring during accumulation of the component lattice points, e.g. due to thermal fluctuations, mechanical stage errors, parasitic vibration, etc. One way of realizing such lattice geometries is, for example, as follows (with reference to FIG. 1):

(1) Orbit the source about the specimen (θ direction) and, during this orbit, take a discrete number of (relatively distal) samplings, at substantially equal arc spacings $\Delta_O$ along the orbit;

(2) For each completed orbit, shift the center of the orbit longitudinally (Z direction), by an amount $\Delta_Z$ that is (roughly) equal to $\Delta_O$ (both $\Delta_O$ and $\Delta_Z$ being measured at the same (orbital) radius from the specimen).

In this regard, it is noted that:

If shift (2) occurs stepwise, after completion of each orbit (1), then one will obtain a lattice such as that illustrated in FIG. 3A or 3B, for example.

On the other hand, if shift (2) occurs continually, during each orbit (1), then one will obtain a lattice such as that illustrated in FIG. 3D, for example.

If $\Delta_Z$ is not exactly (but still roughly) equal to $\Delta_O$, then the unit cell M' in FIG. 3A will be (slightly) rectangular rather than square. Similarly, the parallelogram unit cells M' in FIGS. 3C and 3D will become (slightly) longer along one side relative to a neighboring side.

One can use the previous point to distinguish the invention from the prior art in another way. If, in FIG. 2, a pseudo-unit-cell M" is defined by joining 2×2 neighboring points in adjacent scanning tracts C, then the result will be a (highly) elongate parallelogram—indicative of the excessively high sampling density in one preferential (scanning tract) direction (short side of the parallelogram) and very low sampling density in the area between scanning tracts (long side of the parallelogram).

It should be realized that an actuation scheme such as that set forth in (1)/(2) above is not the only possible way of accruing sample points; for example, one could also use a back-and-forth serpentine scan parallel to the Z direction, combined with a slow rotation about the Z direction. The skilled artisan will grasp that there are many different possibilities in this regard.

In the examples discussed above and illustrated in FIG. 1, the following applies:

The specimen under investigation is elongate along a given longitudinal axis;

The employed reference surface is cylindrical, and is arranged so that its cylindrical axis substantially coincides with said longitudinal axis.

The chosen reference surface could, for example, be a cylinder whose radius is equal to the distance of the source from said longitudinal axis (orbit radius), or it could have a smaller radius, for instance; this is purely a matter of choice, since the cylindrical surface is just virtual/conceptual, and is only used as a reference to help describe the (uniform areal lattice) geometry of the set of intersection points associated with the employed series of viewing axes.

The skilled artisan will understand that the employed reference surface does not necessarily have to be cylindrical, and that one could instead conceive, for example, a (substantially) spherical reference surface, with a (non-elongate) specimen at its center; such a reference surface might be convenient in the case of a specimen and/or detector that could be moved in spherical polar coordinates (R, θ, φ), for example.

A common technique used in tomographic reconstruction is so-called Back Projection (BP). BP is a procedure whereby an image of a specimen, taken along a given viewing axis, is back-projected (smeared out) along that viewing axis, through the specimen. When this is done for several appropriately chosen viewing axes, the various back-projected images will intersect and form a blurry image at the location of the specimen, which blurry image then forms a basis for subsequent reconstructive processing. The present invention allows this procedure to be enhanced, by enabling so-called Back Projection Filtering (BPF), in which a mathematical filtering process is applied to the various line-of-sight images after back projection. Inter alia because of inventive effects (i), (ii) and (iv) above, one has the luxury of being able to apply relatively straightforward space-invariant filters for this purpose; in contrast, the non-uniform/non-isotropic sampling scheme used in conventional helical scans precludes the use of a space-invariant filter, and prior-art approaches would instead have to use far more complicated—and essentially impracticable—space-variant filters if they were to attempt to achieve a similar filtering result. Unlike the prior art, the invention therefore allows back-projected imagery to be easily filtered, e.g. to accentuate certain (higher) frequencies and suppress other (lower) frequencies in Fourier space; this effect can be used to considerably sharpen the back-projected imagery before further reconstruction. Examples of space-invariant filters in the current context include, for instance, the Hilbert transform, Laplace operator, convolution operators, the Median filter, etc.

Care should be taken not to confuse BPF with the similarly-named—but very different—FBP (Filtered Back Projection) technique; in the former, filtering occurs after back projection (in reconstruction/tomographic space), whereas, in the latter, it occurs before back projection (in projection space).

As an alternative and/or supplement to the use of BP, one can instead make use of an iterative reconstruction technique to produce a tomographic image. Examples of such iterative techniques include SIRT (Simultaneous Iterative Reconstruction Technique), ART (Algebraic Reconstruction Technique), DART (Discrete ART), SART (Simultaneous ART), etc. Such iterative techniques (generally) have the advantage of being less noise-sensitive, and of allowing (physical) constraints to be applied to the reconstruction process; however, because they employ several iterations, they tend to be more time-consuming, and to converge relatively slowly. The current invention can mitigate this latter point by—once again—allowing space-invariant filtering to be applied, so as to sharpen-up the outcome of a given iteration before proceeding to the next iteration, thus speeding-up convergence. A particularly effective reconstruction technique in the present invention is MGIR (Multi-Grid Iterative Reconstruction), which starts with a relatively rough-grid construction and progresses iteratively through successively finer grids; when used in conjunction with space-invariant filtering as set forth above, this technique becomes very computationally efficient.

The invention will now be elucidated in more detail on the basis of exemplary embodiments and the accompanying schematic drawings, in which:

FIG. 1 renders a perspective view of a specimen undergoing tomographic imaging, and serves to explain certain (reference) geometric aspects of the current invention.

FIG. 2 renders an unfurled/flattened view of a (cylindrical) feature in FIG. 1, and serves to illustrate a prior-art sampling strategy.

FIG. 3A renders an unfurled/flattened view of a (cylindrical) feature in FIG. 1 (in analogy to FIG. 2), and serves to illustrate a particular embodiment of a sampling strategy according to the present invention.

Figure 4A:
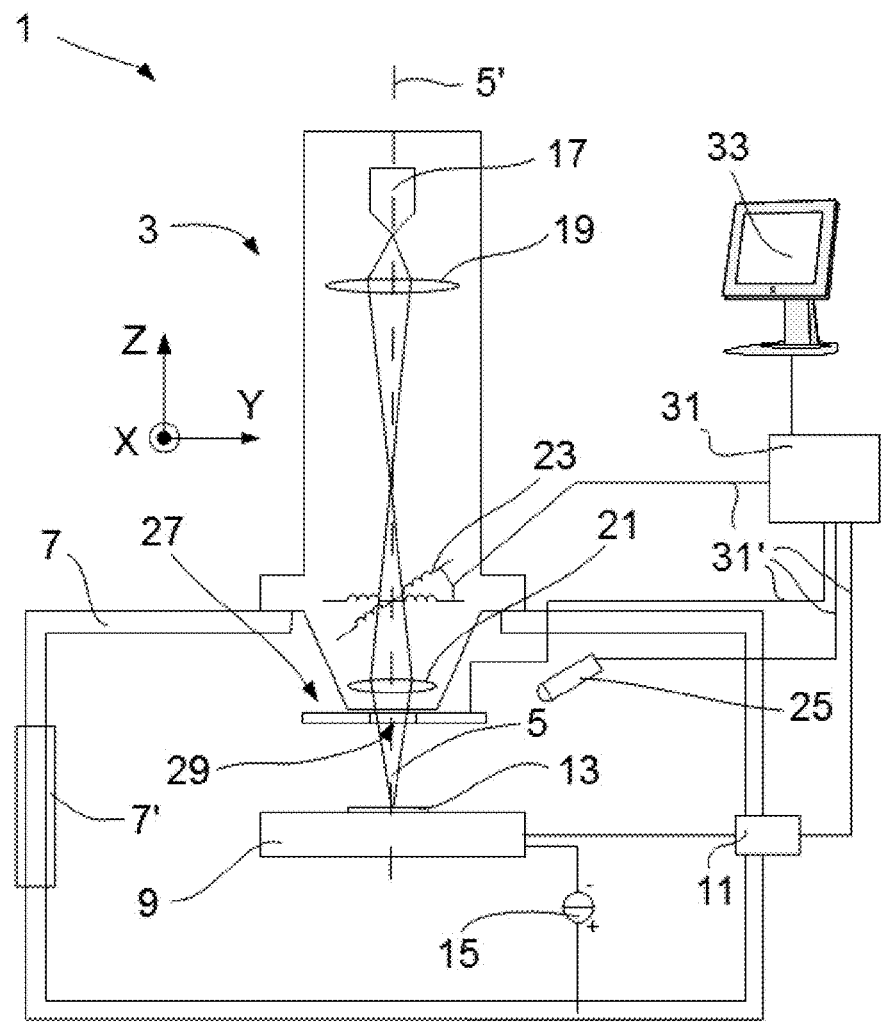

FIG. 4A renders a longitudinal cross-sectional elevation of a particular type of CPM in which an embodiment of the current invention can be carried out using a CT module.

Figure 4B:
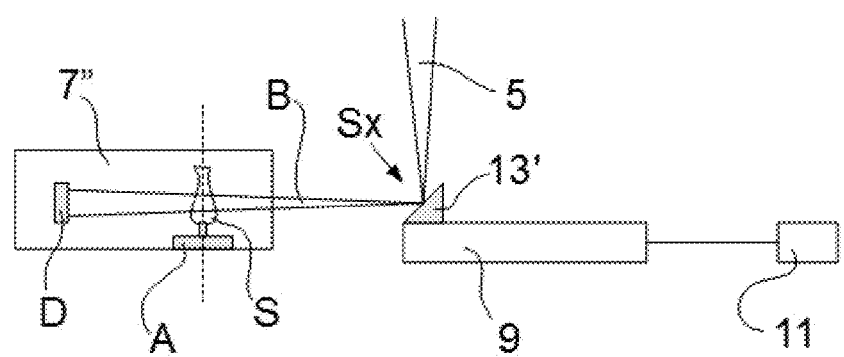

FIG. 4B illustrates a CT module suitable for use in a CPM such as that shown in FIG. 4A.

Embodiment 1

Figure 1:
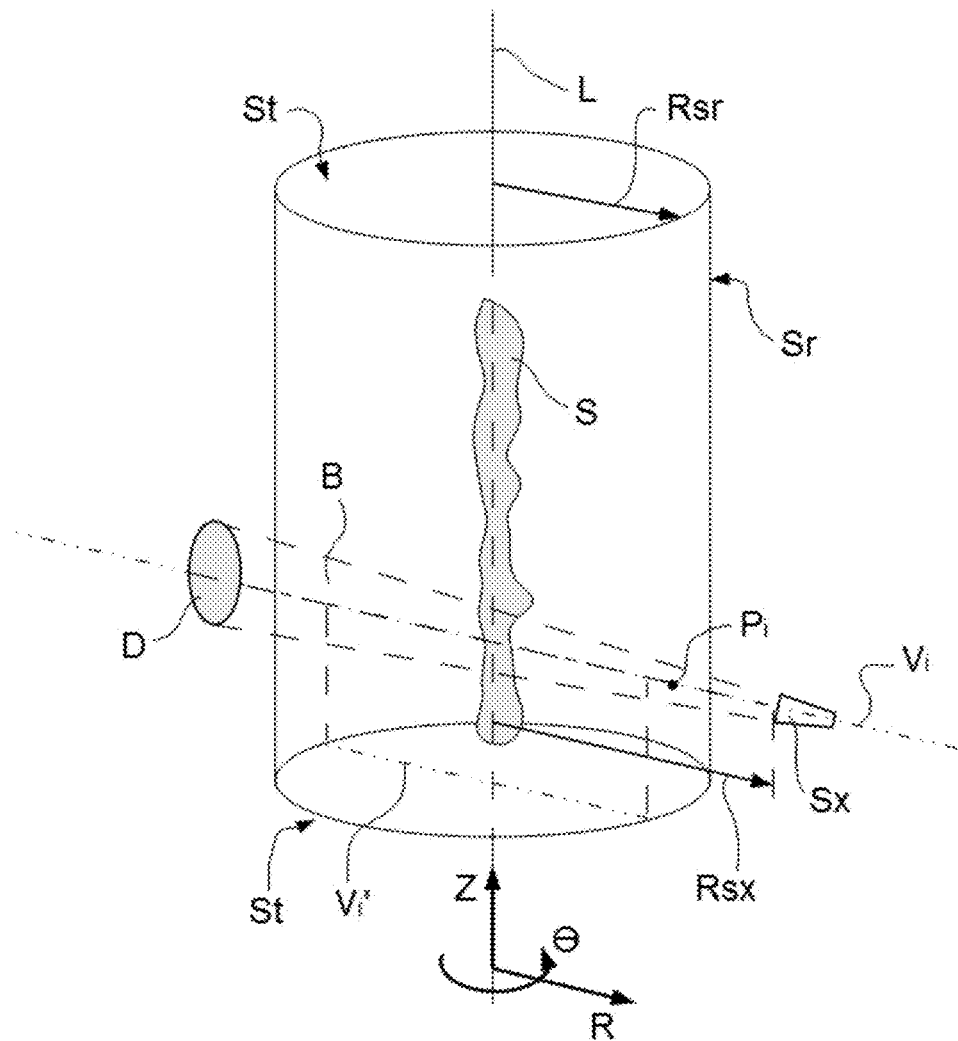

FIG. 1 renders a perspective view of a specimen S undergoing tomographic imaging, and serves to explain certain (reference) geometric aspects of the current invention. In the Figure, an elongated specimen S (which may be macroscopic, micron-scale, or nanometer-scale, for example) has an associated longitudinal axis L. A radiation source Sx produces a beam B of radiation (typically X-rays) that propagates along an axis $V_i$, which may be regarded as a viewing axis or line of sight. As here illustrated, $V_i$ is substantially normal to longitudinal axis L. Having traversed a portion of the specimen S, the beam B impinges upon a (diametrically opposed) detector D, which may, for example, be a Silicon Drift Detector (SDD), Silicon Lithium (Si(Li)) detector, or other suitable detector. The beam B may be regarded as being (for example) cone- or fan-shaped, depending on the effective shape that the detector D "presents" to the source Sx. The detector D forms an electronic image of said portion of the specimen S, which can be stored in an electronic memory. This procedure is then repeated for a series of different viewing axes $V_i$, allowing the specimen S to be viewed along different lines of sight; thereafter, the various images acquired in this manner are used as input to a mathematical reconstruction procedure to produce a tomogram. The various viewing axes $V_i$ are achieved by employing a stage apparatus (not depicted, but see FIG. 4B) to produce relative motion between the source Sx and specimen S, e.g. by producing translational/rotational motion of the source Sx/detector D and/or the specimen S in a predetermined way. Such stage apparatus may, for example, comprise one or more linear motors, piezoelectric actuators, stepper motors, voice coil motors, pneumatic/hydraulic actuators, etc., and can readily be tailored by the skilled artisan to suit the needs of a given setup.

Also shown in the Figure is a virtual reference surface Sr, which, in this case, is a cylindrical surface whose cylindrical axis coincides with longitudinal axis L. This reference surface Sr has a radius Rsr, chosen to be less than or equal to the distance Rsx of the source Sx from the axis L. The viewing axis $V_i$ intersects this reference surface Sr at intersection point $P_i$. Note that, if viewing axis $V_i$ is projected linearly along L, it will coincide with a diameter of a virtual disc-shaped terminal surface St at butt ends of the surface Sr. Associated with the reference surface Sr is a cylindrical coordinate system (R, θ, Z). In FIG. 2 and FIGS. 3A-3D, the reference surface Sr has been unfurled (unwound about L) so as to form a flat surface Sr', with associated planar Cartesian coordinate system (Y, Z), whereby one can take Y=θR.

Figure 2:
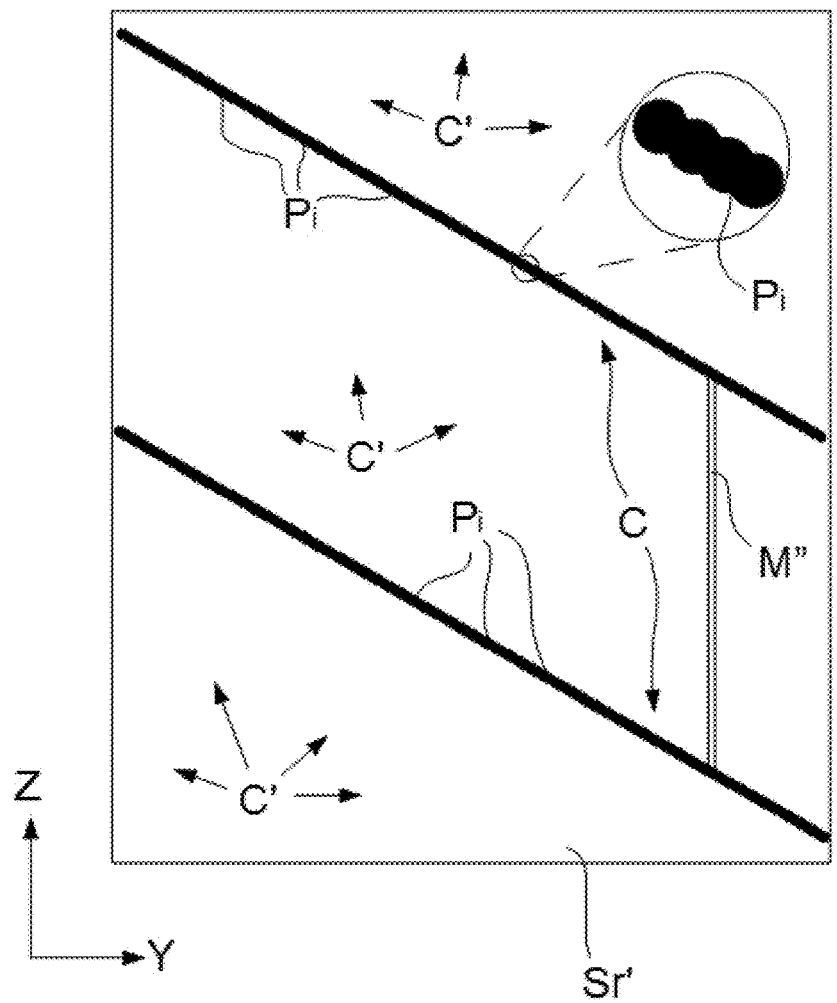

Turning first to FIG. 2, this shows a prior-art situation corresponding to a conventional helical scan, in which the source Sx traces out a helical path relative to the axis L (by concurrently orbiting it about L, and displacing it parallel to L) and images are captured quasi-continuously (i.e. at a high sampling rate) along a succession of closely-separated viewing axes $V_i$. When the resulting helical path on reference surface Sr is unfurled, a result such as that shown in FIG. 2 is obtained, in which trains of closely-spaced intersection points $P_i$ are located along (curvi-)linear tracts C (an exploded partial view at the top right of the Figure illustrates the close spacing of successive points $P_i$). Note the extreme lack of homogeneity/isotropy in this situation: there is a high concentration of points along tracts C (which are highly directional), and no points at all in the intervening regions C'.

Figure 3A:
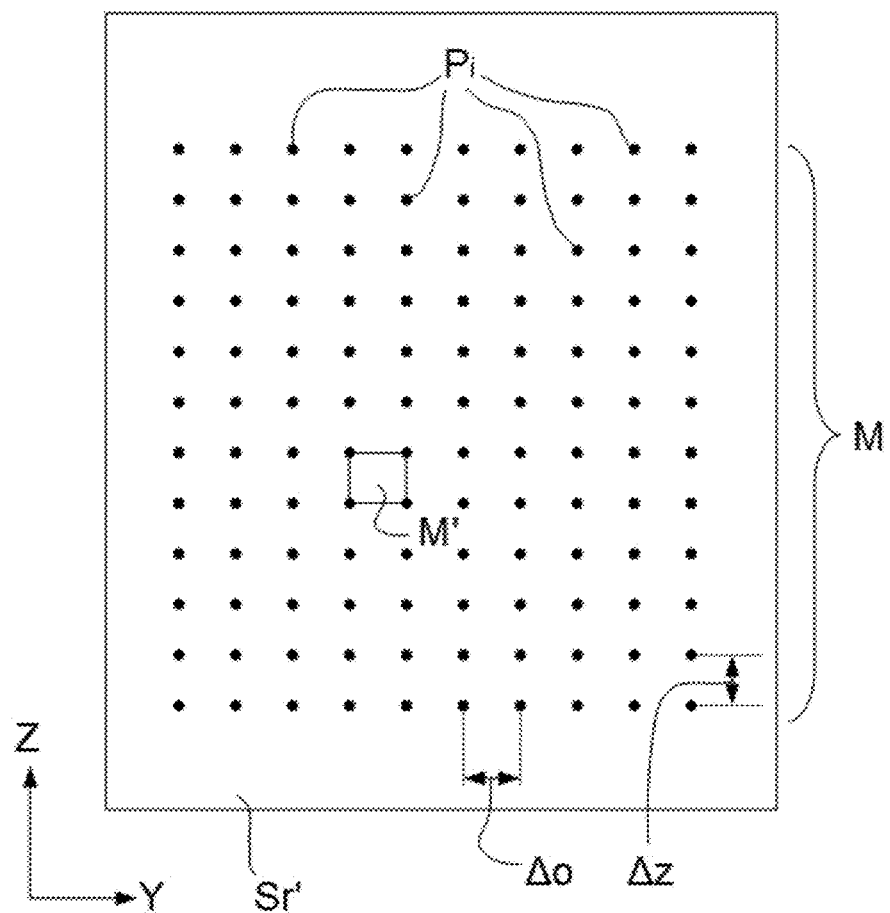
FIG. 3B is similar to FIG. 3A, but differs in that it illustrates a different embodiment of a sampling strategy according to the present invention.
FIG. 3C is similar to FIGS. 3A and 3B, but differs in that it illustrates yet another embodiment of a sampling strategy according to the present invention.
FIG. 3D is similar to FIGS. 3A-3C, but differs in that it illustrates a further embodiment of a sampling strategy according to the present invention.

In stark contrast, FIGS. 3A-3D show distributions of intersection points $P_i$ resulting from embodiments of the present invention. Here, the relative motion of the source Sx and specimen S, and the attendant sampling (image-capture) frequency/intervals, are chosen so as to yield a two-dimensional lattice (matrix, net) M of points $P_i$ located areally on (at least part of) surface Sr in a substantially uniform distribution. Associated with this lattice M is a unit cell M', which can be regarded as a repeating fundamental "building block" of the lattice M. Note that:

(A) in FIG. 3A, the matrix M is substantially orthogonal, and the unit cell M' is a rectangle, which is essentially a square in the current situation. Such a pattern can, for example, be achieved by repeating the following steps:
  Orbiting the source Sx about the line L in a horizontal orbital plane (normal to L), and taking equi-spaced samplings along this orbit at linear intervals $\Delta_O$. In FIG. 3A, there are ten points $P_i$ along each horizontal row (Y row), meaning that $\Delta_O=(2\pi/10)\times Rsr$.
  After completion of each such circular orbit, displacing the orbital plane along the axis L by an amount $\Delta_Z \approx \Delta_O$ (with Rsr≈Rsx).
In a particular, non-limiting example, each of $\Delta_Z$ and $\Delta_O$ is of the order of about 50 μm in the case of imaging a 5-mm-diameter specimen in a micro CT.

Figure 3B:
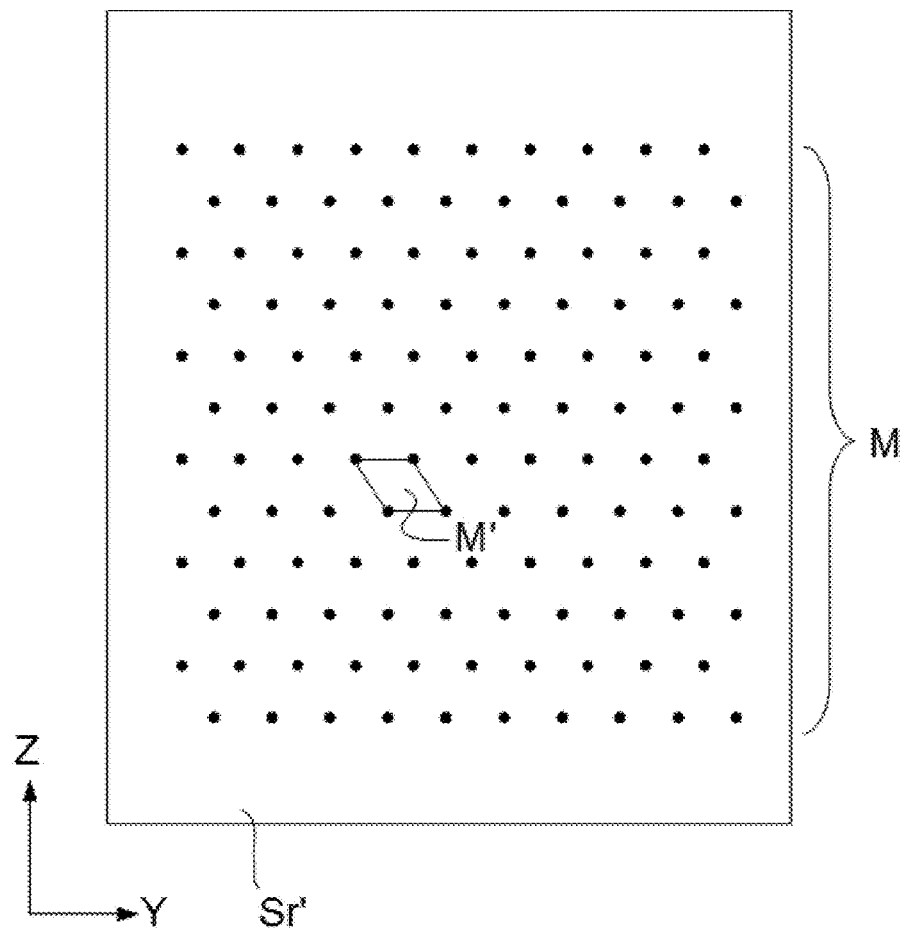

(B) The situation in FIG. 3B is largely identical to that in FIG. 3A, except in that the matrix M is now a staggered orthogonal matrix (or, alternatively, a trigonal or hexagonal matrix), with a unit cell M' that is a parallelogram (with substantially equal adjacent side lengths in the current situation). Such a pattern can be produced in the same way as that of FIG. 3A, except in that successive horizontal rows of points $P_i$ are Y-shifted (by an amount $\Delta_O/2$ in the current situation).

Figure 3C:
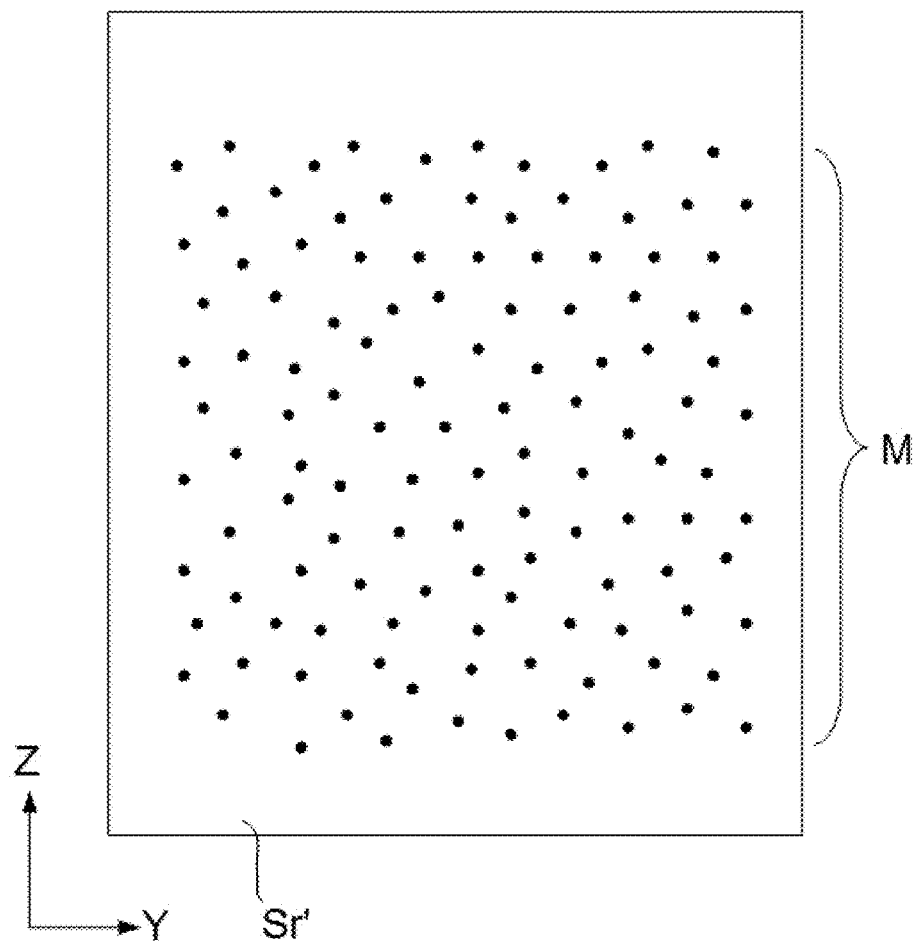

(C) Whereas the lattice patterns M in FIGS. 3A and 3B are regular, the lattice pattern M in FIG. 3C is irregular (quasi-random)—but nevertheless substantially uniform. There is no meaningful unit cell in this situation, but the distribution is still roughly homogeneous, on a relatively zoomed-out scale. Such a pattern can, for example, be produced using the technique in (A), except in that:

Sampling points in a given orbit are not necessarily equi-spaced along that orbit;

Small Z positional adjustments can be made (up or down) in the course of an orbit.

In this way, the pattern in FIG. 3C can be seen as an on-the-fly-distorted rendition of the pattern in FIG. 3A.

Figure 3D:
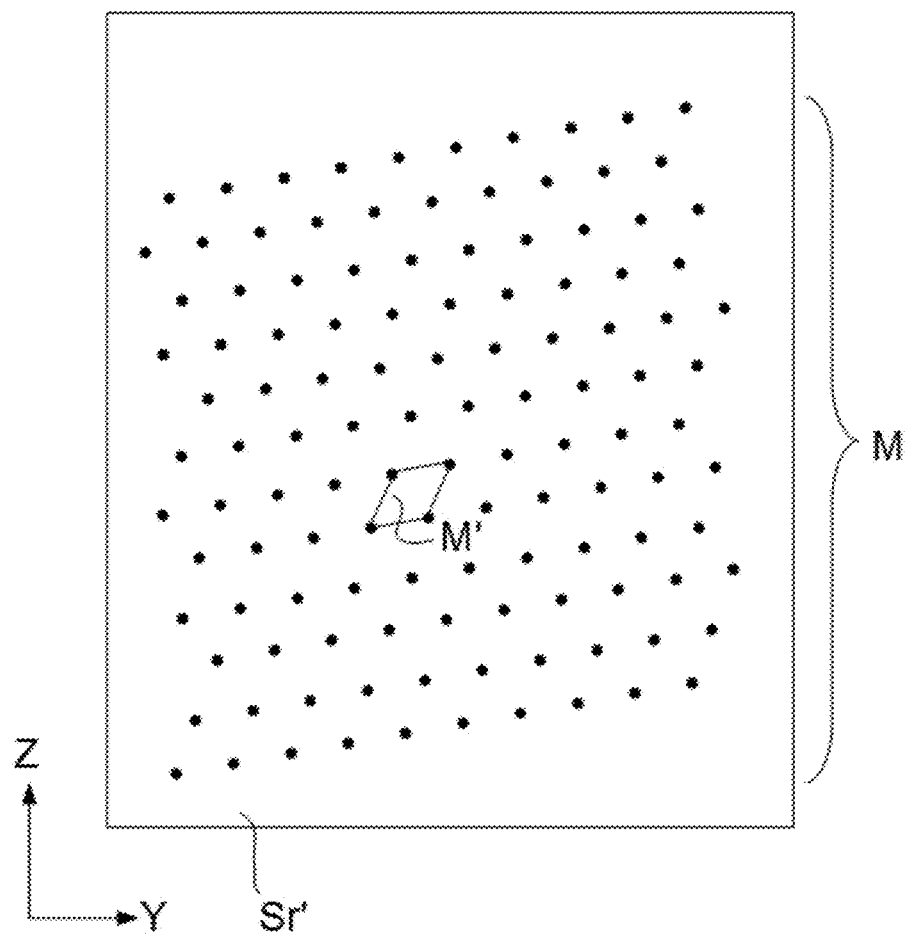

(D) The situation in FIG. 3D is largely identical to that in FIG. 3A, except in that the matrix M is now a sheared orthogonal matrix, with a unit cell M' that is a canted parallelogram (once again with substantially equal adjacent side lengths in the current situation). Such a pattern can be produced in the same way as that of FIG. 3A, except in that the Z-shift is performed continuously during the orbital motion. This produces a helical motion, but the distance between successive sampling points along the helix is matched to the Z-spacing of successive windings in the helix, leading to a much more uniform distribution of points than in the prior-art case of FIG. 2B (effectively producing a form of "sparse helix"). For comparison purposes, a pseudo-unit-cell M'' has been drawn in FIG. 2, which joins:

A first pair of adjacent sampling points along the direction of upper tract C;

A second pair of adjacent sampling points along the direction of lower tract C, located directly below (and joined in the Z direction to) said first pair.

The result is a very elongated rectangle, whose width (normal to Z) is much smaller than its length (along Z). The severe elongation of this rectangle M'' is associated with the highly non-uniform distribution of sampling points $P_i$ in FIG. 2.

Embodiment 2

FIG. 4A is a highly schematic depiction of an embodiment of a CPM 1 that can be used in conjunction with the present invention; more specifically, it shows an embodiment of a SEM—though, in the context of the current invention, it could just as validly be an ion-based microscope, for example, or a TEM, for instance. The microscope 1 comprises a particle-optical column/illuminator 3, which produces a beam 5 of charged particles (in this case, an electron beam) that propagates along a particle-optical axis 5'. The particle-optical column 3 is mounted on a vacuum chamber 7, which comprises a specimen holder 9 and associated stage/actuator 11 for holding/positioning a specimen 13. The vacuum chamber 7 is evacuated using vacuum pumps (not depicted). With the aid of voltage source 15, the specimen holder 9, or at least the specimen 13, may, if desired, be biased (floated) to an electrical potential with respect to ground.

The particle-optical column 3 comprises an electron source 17 (such as a Schottky emitter), (electrostatic/magnetic) lenses 19, 21 (in general, more complex in structure than the schematic depiction here) to focus the electron beam 5 onto the specimen 13, and a deflection unit 23 to perform beam deflection/scanning of the beam 5. When the beam 5 impinges on/is scanned across the specimen 13, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, 25, 27, which may, for example, be embodied as follows:

Detector 25 may, for example, be an electron detector (such as an Solid State Photo-Multiplier), X-ray detector (such as an SDD or Si(Li) sensor) or a light detector (such as a photodiode).

Detector 27 is a segmented electron detector, comprising a plurality of independent detection segments (e.g. quadrants) disposed about a central aperture 29 (allowing passage of the beam 5). Such a detector can, for example, be used to investigate (the angular dependence of) a flux of output (secondary or backscattered) electrons emerging from the specimen 13.

These are just examples, and the skilled artisan will understand that other detector types, numbers and geometries/configurations are possible.

The microscope 1 further comprises a controller/computer processing unit 31 for controlling inter alia the lenses 19 and 21, the deflection unit 23, and detectors 25, 27, and displaying information gathered from the detectors 25, 27 on a display unit 33 (such as a flat panel display); such control occurs via control lines (buses) 31'. The controller 31 (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

Also depicted is a vacuum port 7', which may be opened so as to introduce/remove items (components, specimens) to/from the interior of vacuum chamber 7, or onto which, for example, an ancillary device/module may be mounted (not depicted). A microscope 1 may comprise a plurality of such ports 7', if desired.

In the context of the current invention, the microscope 1 can also comprise an in situ CT module 7'' as shown in FIG. 4B. In this figure, the CPM's specimen holder 9 has been provided with a metal target 13', which is positioned (using actuator 11) so that electron beam 5 impinges upon it, thus producing Bremsstrahlung X-rays in a variety of directions. The Figure shows a beam B of such X-rays that propagate to one side from target 13' (effective source Sx) into module 7'', where they pass through a specimen S and impinge upon a detector D: compare to FIG. 1. The specimen S is mounted on a stage apparatus A that allows the specimen S to be positioned/moved (typically translated and rotated) relative to the source Sx.

Such a CT module 7'' may be permanently present (ab initio) in the vacuum enclosure 7, or it may be an add-on module that can be mounted (post-manufacture of the CPM 1) on/within a spare vacuum port 7', for example.

The invention claimed is:

1. A method of investigating a specimen using a tomographic imaging apparatus comprising:
   a specimen holder, for holding the specimen;
   a source, for producing a beam of radiation that can be directed at the specimen;
   a detector, for detecting a flux of radiation transmitted through the specimen from the source;
   a stage apparatus, for producing relative motion of the source with respect to the specimen, so as to allow the source and detector to image the specimen along a series of different viewing axes; and
   a processing apparatus, for assembling output from the detector into a tomographic image of at least part of the specimen, the method comprising:
   determining a virtual reference surface that surrounds the specimen and is substantially centered thereon;
   determining an incoming point of intersection of each of said viewing axes with this reference surface, thereby generating a set of such intersection points corresponding to said series of viewing axes;
   determining discrete viewing axes in said series so as to cause said set to comprise a two-dimensional lattice of points located areally on said reference surface in a substantially isotropic distribution;
   directing the beam of radiation along each of the discrete viewing axes;
   detecting the flux of radiation transmitted through the sample along each of the discrete viewing axes; and
   assembling output from the detector into a tomographic image of at least part of the specimen.

2. A method according to claim 1, wherein the determined series of viewing axes results in a substantially shift-invariant imaging Point Spread Function and in which assembling output from the detector into a tomographic image comprises applying a space invariant filter to the reconstructed tomographic volume image after a back-projection.

3. A method according to claim 1, wherein at least part of said lattice of points has a geometry selected from the group consisting of:
   an orthogonal array;
   a skewed orthogonal array;
   a staggered orthogonal array;
   a hexagonal array,
   and combinations hereof.

4. A method according to claim 1, wherein at least part of said lattice of points has a non-regular geometry.

5. A method according to claim 1, wherein:
   said specimen is elongate along a given longitudinal axis;
   said reference surface is cylindrical, and is arranged so that its cylindrical axis substantially coincides with said longitudinal axis.

6. A method according to claim 1, wherein said processing apparatus employs a Back Projection technique in combination with post-Back-Projection space-invariant filtering in producing said tomographic image.

7. A method according to claim 1, wherein said processing apparatus employs a Multi-Grid Iterative Reconstruction technique in producing said tomographic image.

8. A method according to claim 2, wherein at least part of said lattice of points has a geometry selected from the group consisting of:
   an orthogonal array;
   a skewed orthogonal array;
   a hexagonal array,
   and combinations hereof.

9. A method according to claim 2, wherein said processing apparatus employs a Back Projection technique in combination with post-Back-Projection space-invariant filtering in producing said tomographic image.

10. A method according to claim 3, wherein said processing apparatus employs a Back Projection technique in combination with post-Back-Projection space-invariant filtering in producing said tomographic image.

11. A method according to claim 3, wherein:
    said specimen is elongate along a given longitudinal axis;
    said reference surface is cylindrical, and is arranged so that its cylindrical axis substantially coincides with said longitudinal axis.

12. A method according to claim 11, wherein said processing apparatus employs a Back Projection technique in combination with post-Back-Projection space-invariant filtering in producing said tomographic image.

13. A method according to claim 11, wherein said processing apparatus employs a Multi-Grid Iterative Reconstruction technique in producing said tomographic image.

14. The method of claim 1 in which determining discrete viewing axes in said series so as to cause said set to comprise a two-dimensional lattice of points located areally on said reference surface in a substantially isotropic distribution comprises determining discrete viewing axes in said series so as to cause said set to comprise a two-dimensional lattice of points located areally on said reference surface in a sufficiently isotropic distribution that assembling output from the detector into a tomographic image of at least part of the specimen can apply space-invariant filtering of after back projection.

15. The method of claim 1 in which the directing the beam of radiation along each of the discrete viewing axes comprises directing the beam along a trajectory that is neither a spiral nor a circle and includes directing the beam to points that are not clustered around a circular or spiral pattern.

16. The method of claim 1 in which the directing the beam of radiation along each of the discrete viewing axes includes directing the beam to points that are not clustered around a circular or spiral pattern.

17. The method of claim 1 in which assembling output from the detector into a tomographic image of at least part of the specimen comprises performing a back-projection operation or an iterative reconstruction using the flux of radiation transmitted along each of the substantially isotropic distributed discrete viewing axes.

18. A tomographic imaging apparatus comprising:
    a specimen holder, for holding a specimen;
    a source, for producing a beam of radiation that can be directed at the specimen;
    a detector, for detecting a flux of radiation transmitted through the specimen from the source;
    a stage apparatus, for producing relative motion of the source with respect to the specimen, so as to allow the source and detector to image the specimen along a series of different viewing axes;
    a processing apparatus, for assembling output from the detector into a tomographic image of at least part of the specimen said processing apparatus is programmed to:
    adopt a virtual reference surface that surrounds the specimen and is substantially centered thereon;
    determine an incoming point of intersection of each of said viewing axes with this reference surface, thereby generating a set of such intersection points corresponding to said series of viewing axes; and
    choose discrete viewing axes in said series so as to cause said set to comprise a two-dimensional lattice of points located areally on said reference surface in a substantially isotropic distribution.

19. A charged-particle microscope comprising a tomographic imaging apparatus as claimed in claim 18.

20. A method of investigating a specimen using a tomographic imaging apparatus comprising:
- a specimen holder, for holding the specimen;
- a source, for producing a beam of radiation that can be directed at the specimen;
- a detector, for detecting a flux of radiation transmitted through the specimen from the source;
- a stage apparatus, for producing relative motion of the source with respect to the specimen, so as to allow the source and detector to image the specimen along a series of different viewing axes; and
- a processing apparatus, for assembling output from the detector into a tomographic image of at least part of the specimen, the method comprising:
- determining a virtual reference surface that surrounds the specimen and is substantially centered thereon;
- determining an incoming point of intersection of each of said viewing axes with this reference surface, thereby generating a set of such intersection points corresponding to said series of viewing axes;
- determining discrete viewing axes in said series so as to cause said set to comprise a two-dimensional lattice of points located areally on said reference surface in a substantially isotropic distribution;
- directing a beam of radiation from the source along the viewing axes;
- detecting a flux of radiation transmitted through the specimen from the source; and
- reconstructing a three-dimensional image of the specimen from the radiation flux detected along the viewing axes.

* * * * *